US 7,029,445 B2

(12) United States Patent
Shinomura et al.

(10) Patent No.: US 7,029,445 B2
(45) Date of Patent: Apr. 18, 2006

(54) ULTRASONIC DIAGNOSING APPARATUS

(75) Inventors: Ryuichi Shinomura, Higashimatsuyama (JP); Yuichi Miwa, Kokubunji (JP); Hirotaka Baba, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/169,979

(22) PCT Filed: Jan. 12, 2001

(86) PCT No.: PCT/JP01/00111

§ 371 (c)(1),
(2), (4) Date: Nov. 3, 2004

(87) PCT Pub. No.: WO01/50961

PCT Pub. Date: Jul. 19, 2001

(65) Prior Publication Data

US 2005/0075570 A1    Apr. 7, 2005

(30) Foreign Application Priority Data

Jan. 12, 2000    (JP) .............................. 2000-003727

(51) Int. Cl.
*A61B 8/00*    (2006.01)
(52) U.S. Cl. ...................... 600/443; 600/447; 600/459
(58) Field of Classification Search ........ 600/437–472; 367/7, 11, 130, 138; 128/916; 73/625, 626
See application file for complete search history.

(56) References Cited

U.S. PATENT DOCUMENTS 4,641,660 A * 2/1987 Bele ........................... 600/459

FOREIGN PATENT DOCUMENTS

JP            08317923 A * 12/1996

* cited by examiner

*Primary Examiner*—Ali Imam
(74) *Attorney, Agent, or Firm*—Antonelli, Terry, Stout and Kraus, LLP.

(57) ABSTRACT

An ultrasonic diagnostic apparatus transmits an ultrasonic beam into an object to be examined using a multi-ring arrangement formed with transducer elements arrayed two-dimensionally in concentric rings and receives an echo so as to create a tomogram or a three-dimensional image of the object. To correct for focusing error due to the difference in length of ultrasound propagating paths, the ultrasonic diagnostic apparatus groups the transducer elements so as to form a multi-ring arrangement, transmits/receives ultrasonic beams with a delay to each ring of the multi-ring arrangement and scans the ultrasonic beam so as to create an ultrasonic image, measures delay error due to presence of a sound speed non-uniformity portion of the object and changes either the coupling of the multi-ring or the delay time based on the measurement error.

12 Claims, 6 Drawing Sheets

ULTRASONIC DIAGNOSING APPARATUS

CROSS REFERENCE TO RELATED APPLICATIONS

This application is the U.S. National Phase under 35 U.S.C. §371 of International Application PCT/JP01/00111, filed Jan. 12, 2001, which was published in a language other than English which claims priority of JP 2000-3727, filed Jan. 12, 2000. Each of the above applications is incorporated herein by reference in their entirety.

FIELD OF THE INVENTION

The present invention relates to an ultrasonic diagnostic apparatus of the type used for acquiring an ultrasonic image of a diagnostic part by scanning the interior of an object to be examined in real time with an ultrasonic beam formed with a two-dimensional transducer array; and, more particularly, the invention relates to an ultrasonic diagnostic apparatus which includes means for correcting a focusing error which occurs due to a difference in the length of propagating paths of ultrasound transmitted/received with a multi-ring type transducer in which a plural number of electronically transducers are bundled into concentric rings.

BACKGROUND OF THE INVENTION

An apparatus having a plural number of transducer composed of a two-dimensional transducer array in which sector scanning is performed using an ultrasonic beam (in an arbitrary direction) generated by a transmitting/receiving circular pattern of transducers formed in the two-dimensional transducer array is known. In this ultrasonic diagnostic apparatus, for example, if 64×64 transducers are disposed in the two-dimensional array, then the total number of transducers is 4,0967; and, ultrasonic scanning is performed with a separate delay control provided for each transducer element. In this case, a beam-forming circuit with 4,096 channels is necessary. Realizing a beam-forming circuit having such a large number of multi-channel delay circuits is difficult. So, by thinning out the number of driven elements for forming one ultrasonic beam, the number of delay circuit channels in the beam-forming circuit is reduced. But the S/N of signal acquired by thinning out the driven elements is deteriorated. So, the apparatus is realized by comprising a beam-forming circuit having as many as delay channels possible. For example, there is an apparatus that comprises a beam-forming circuit having a delay circuit of 256 channels for transmitting and 256 channels for receiving.

As shown in FIG. 4, a linear scanning expanded field of view obtained by moving the transmitting/receiving circular pattern of transducer elements 1, that are arrayed in a two-dimensional X, Y direction, and a scanning method in which a convex scanning is applied to two-dimensions are proposed. In this case, the number of transducer elements 1 is more than in said sector scanning type apparatus. So, for reducing the number of channels in the beam-forming circuit, an apparatus is known that produces an ultrasound transmitting/receiving circular pattern 2 by electronically bundling a plural number of transducer elements 1 in the two-dimensional array into a multi-ring arrangement with concentric rings, so as to give a consistent delay time to the transducer elements composing one ring of said multi-ring arrangement. The apparatus transmits/receives an ultrasonic beam with a delay time between rings, and forms an ultrasonic image by moving said circular pattern 2 in X, Y directions.

As shown in FIG. 5, in said multi-ring arrangement, each ring is formed by the bundling of transducer elements in concentric rings of which the distance $L_1, L_2 \ldots$, from the single focal spot F is almost the same, and the diameter of the most exterior ring is diameter 2 for ultrasound transmitting/receiving. In this method, the bundling of transducer elements in concentric rings makes it possible to reduce greatly the number of channels in the beam forming circuit, which corresponds to the number of delay circuits, and the S/N of a signal acquired by using all elements in a circular pattern can be improved.

When considering the shape of an ultrasonic beam, a focusing calculation for an ultrasonic beam in the object to be examined is traditionally performed under the condition that the speed of sound in an ultrasonic propagation medium is uniform. As shown in FIG. 6, a traditional apparatus comprises delay circuits 4, 4, . . . comprising one per transducer element of the probe 3 having a plural number of transducers and an adder 5 for adding received signals output from these delay circuits 4, 4, . . . . Although reflected signals from focus point 6 in the object propagate through medium 7 to reach each transducer element, the difference in the path length from the focus point to each transducer element causes a difference in the arrival time of each reflected signal. In this case, the reflected signals reach the transducer elements located in the center of probe 3 early, and, on the other hand, they reach the transducer elements at the ends late. So, the shape of the wave surface 8 in the received signals is not linear. Thus, the signals output from transducer elements in the center part of the probe are delayed with a large amount of delay time in delay circuits 4 corresponding to each received signal, and the signals output from transducer elements at the ends of the probe are delayed with a small amount of delay time. The signals are then output to adder 5. With these delay operations, the wave surface 9 of the signal output from delay circuits 4 is linear since the signals have the same phase. The received signals having the same phase, such as shown by wave surface 9 in this condition, are added in adder 5 so as to form the combined signal 10.

But actually, as shown in FIG. 7, a sound speed non-uniformity part 11 typically exists on the path from the focus point 6 in the object to the probe 3, so that the wave surface of the received signal is disturbed, as shown at 8'. In this case, when performing the delay operation, while assuming that the speed of sound is uniform, the wave surface of the received signals output from delay circuits 4 is distorted. as shown at 9', so that they do not have the same phase. Accordingly. the output produced in adder 5 does not increase in intensity as the signals are added, so that its intensity is small, as shown by signal 10'.

On the contrary, there is a technology referred to as an adaptive ultrasonic imaging method which operates to correct the delay amount produced in said delay circuits 4 in accordance with the speed of sound in the medium. In the adaptive ultrasonic imaging technology, a mutual correlation method for correcting the delay amount by correction processing of respectively received signals between adjacent channels, and a maximum value brightness method for searching for a brightness maximum while changing the delay amount of the delay circuits are known.

FIG. 8 is a block diagram which illustrates the mutual correlation method. In FIG. 8, a signal received from each transducer element, which is not shown in the figure, is delayed by a predetermined amount by a respective delay circuit 4, 4, .... This delay is possible by use of analog delay circuits or digital delay circuits. In this case, when outputs of adjacent channels in each transducer element, a mutual correlation processing is carried out with correlation device 12, and the phase difference between the outputs of adjacent channels can be obtained. By detecting the phase difference value, transforming it to focus data in correction processing part 13, and feeding the transformed data back to focus controlling part 14, the delay amount produced by the individual delay circuits 4 can be corrected.

FIG. 9 is a block diagram illustrating the maximum value brightness method. In FIG. 9, a received signal from each transducer element, which is not shown in the figure, is delayed in a respective delay circuit 4, 4, ... by a predetermined amount. The outputs delayed in the respective delay circuits 4, 4, ... are added in adder 5., and this output is input to maximum value detecting part 15. This maximum value detecting part 15 compares the input signal with the last input value, and, in case the input value is smaller than the last detected value, the focus data is slightly changed systematically in focus controlling part 14. Then, after the phasing of the received echo signal has been changed by this focus data, the output of adder 5 is inputted to the maximum value detecting part 15, and judged again. After repeating this operation, when the detected value is formed to converge at the maximum value, its data is used as focus data.

However, as shown in FIG. 4 and FIG. 5, in an ultrasonic diagnostic apparatus in which a transmitting/receiving circular pattern 2 is formed by bundling transducer elements of a two-dimensional array into concentric rings to compose a multi-ring arrangement, in case there is a sound speed non-uniformity part 11 on the path from focus point 6 to the probe 3 in the object, since transducer elements 1 in the two-dimensional array are bundled in concentric rings as thus described, it is difficult to detect the phase difference due to said path difference for correcting for the influence of said sound speed non-uniformity part 11. Therefore, the phase difference of echo signals caused by said path difference, due to the existence of the sound speed non-uniformity part 11, is not corrected. As a result, the image quality is deteriorated because the ultrasonic beam becomes worse.

Thus, it is an object of the present invention to solve the above-mentioned problems by providing an ultrasonic diagnostic apparatus which is able to correct a focusing error by detecting the phase difference of echo signals which occur due to a difference in the ultrasonic propagating path, even when its multi-ring arrangement of transducers is composed by bundling transducers in a two-dimensional array for transducer elements in concentric rings.

SUMMARY OF THE INVENTION

To achieve the foregoing object, an ultrasonic diagnostic apparatus is provided in accordance with the present invention, in which there is a probe comprising a plural number of transducer elements formed as a two-dimensional array for transmitting/receiving an ultrasound to an object to be examined. A circular pattern of transducers for ultrasound transmitting/receiving is formed by bundling said two-dimensional array of transducer elements in concentric rings to form a multi-ring arrangement, and transmitting/receiving of an ultrasound is achieved with the application of a delay between each ring in said multi-ring arrangement, so that an ultrasonic image is formed by scanning said beam. The ultrasonic diagnostic apparatus comprises means for measuring focusing error that is produced due to a sound speed non-uniformity in said object and for transmitting/receiving an ultrasonic beam that has been corrected based on the measured error by changing at least one of the bundling of said multi-ring arrangement of transducers or the delay time, and means for imaging the object by using an echo signal of the corrected ultrasonic beam.

In the apparatus of the present invention, the circular pattern formed by said multi-ring arrangement, in which transducer elements in the two-dimensional array are bundled in concentric rings in said probe is divided into a plural number of sections in a radial form from the center to the outside thereof. And, the focusing error due to a sound speed non-uniformity in the object is measured between the ring sectors of each divided section and between each section, and the ultrasonic beam is corrected by feeding this measured value back to the delay circuits.

Furthermore, in the apparatus of the present invention, a bundled arrangement of transducer elements form a circular pattern that is different from that of said multi-ring arrangement composed by bundling said transducer elements of a two dimensional array in said probe in concentric rings. And, the focusing error due to a sound speed non-uniformity in the object between each sector is measured, and the ultrasonic beam is corrected by feeding back this measured value to the delay circuits and returning the form of the multi-ring to an initial setting.

THE BEST MODE FOR CARRYING OUT THE INVENTION

Hereinafter, an embodiment of the present invention will be described in detail based on the accompanying drawings.

Figure 1:
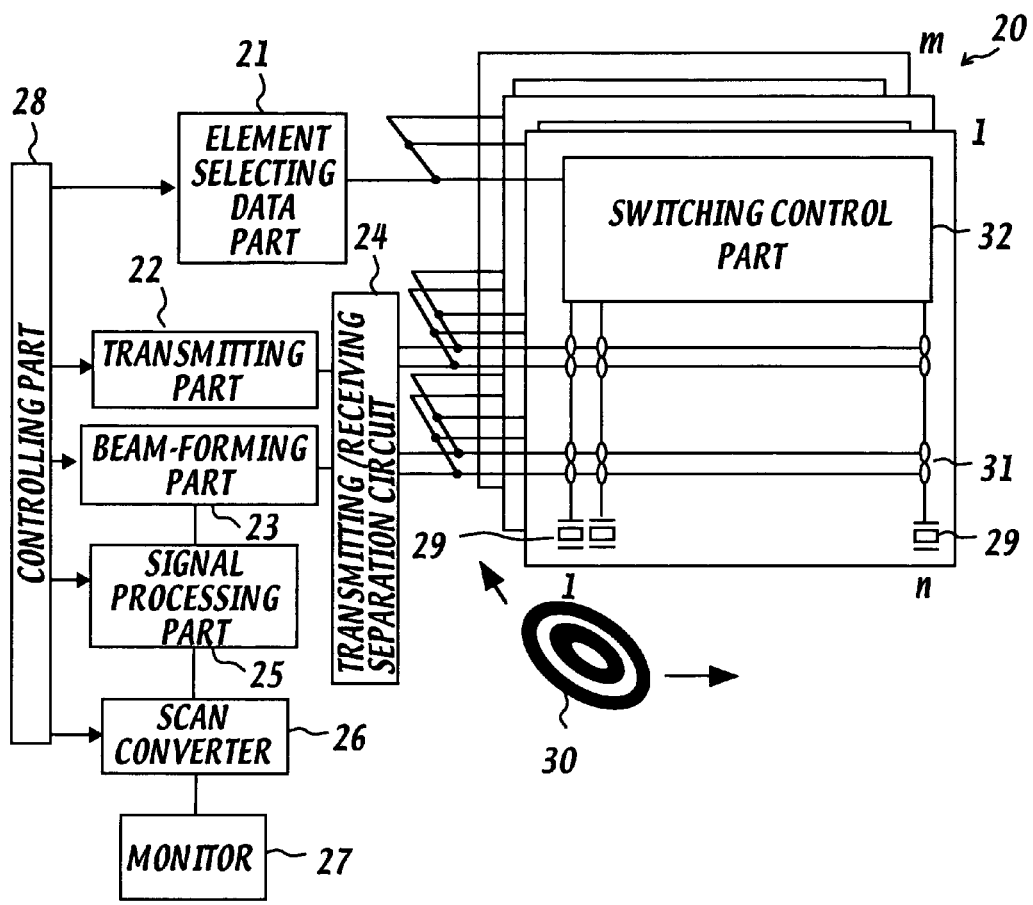
FIG. 1 is a block diagram showing the overall arrangement of an embodiment of an ultrasonic diagnostic apparatus according to the present invention.

FIG. 1 is a block diagram showing an embodiment of an ultrasonic diagnostic apparatus according to the present invention. This ultrasonic diagnostic apparatus forms an ultrasonic beam with a two-dimensional transducer array and acquires an ultrasonic image of a diagnostic part in the interior of an object to be examined by scanning an ultrasonic beam over the object in real time. As shown in FIG. 1, it comprises a probe 20, an element selecting data part 21, a transmitting part 22, a beam-forming part 23, a transmitting/receiving separation circuit 24, a signal processing part 25, a scan converter 26, a monitor 27, and a controlling part 28.

Figure 4:
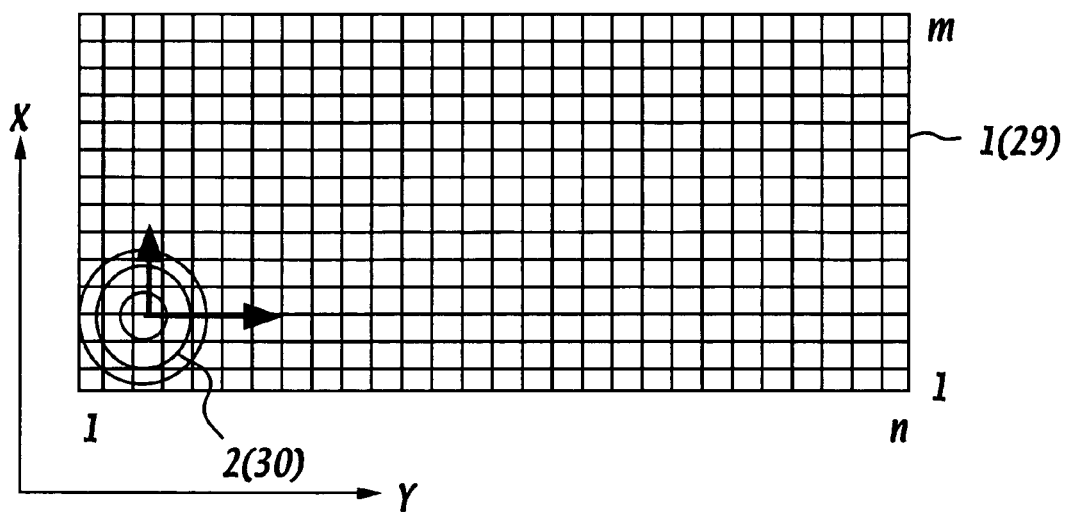
FIG. 4 is a diagrammatic plan view showing an example in which a multi-ring arrangement is set to probe in accordance with the present invention or in a traditional ultrasonic diagnostic apparatus, and in which transmitting and receiving of an ultrasonic beam and two-dimensional scanning are performed.

The probe 20 transmits an ultrasound to an object to be examined and receives its echo. It is composed of a plural number of transducer elements 29, 29, arrayed two-dimensionally. These transducer element 29, 29, . . . are arrayed two-dimensionally such as 1~m in the x direction and 1~n in the y direction in planar view, as shown in FIG. 4. And, the transducer elements 29, that are arrayed two-dimensionally, are also bundled electronically to form a multi-ring arrangement in which there are concentric rings, and the multi-ring arrangement has the form of an ultrasonic transmitting/receiving circular pattern 30. A delay time is given between each ring of said multi-ring arrangement to transmit and receive the ultrasonic beam. The ultrasonic beam scanning is performed by moving said circular pattern 30 at each cycle of the transmitting/receiving of the ultrasound, whereby an ultrasonic image is formed. In addition, said multi-ring arrangement is made, for example, with fresnel-bundles.

In addition, connection switch groups 31 are connected for coupling an arbitrary delay channel in the beam-forming circuits to be described in later to selected transducer elements. Furthermore, a switching control part 32 for controlling the switching operation is connected to the connection switch groups 31.

Element selecting data part 21 memorizes element selecting data needed to form the transmitting/receiving circular pattern 30. In this regard, element selecting data read out from element selecting data part 21 is transferred to switching control part 32; and, by controlling said switching control part 32, the switching on and off of connection switch groups 31 is controlled to form the transmitting/receiving circular pattern 30.

Transmitting part 22 supplies a transmitting signal for emitting an ultrasound to the respective ultrasonic transducer elements with the application of a delay time such that the ultrasound transmitted from each transducer element which forms the transmitting/receiving circular pattern 30 of said probe 20 is focused at a desired focus point set in the object. The beam-forming part 23 performs a desired focus process on respective reflected echo signals received by the transducer elements 29 of said probe 20 and forms a receiving beam by phasing and adding these echo signals. The transmitting/receiving separation circuit 24 changes the connection of said transmitting part 22 and beam-forming part 23 to selected transducer elements 29 to control whether an ultrasound is transmitted or received.

Signal processing part 25 inputs the signal output from said beam-forming part 23 and obtains the data of one scanning line by predetermined processing, such as detecting, compression, filtering processing, edge emphasizing etc. The scan converter 26 inputs the data output from said signal processing part 25 and forms image data for display on the monitor 27, and it also performs scan conversion between ultrasonic scanning and scanning for display and interpolation processing of image data or the like. Furthermore, monitor 27 displays the data received from said scan converter 26 as an ultrasonic image. On the display screen, a three-dimensional image or an arbitrary slice image is displayed. Controlling part 28 controls the operation of each element.

In accordance with the present invention, means is provided for measuring a delay error in receiving a signal due to the presence of a sound speed non-uniformity part in said object, and for correcting either the bundling of transducer elements in the multi-ring arrangement or the delay time or both.

In a first embodiment, the circular pattern 30, composed of the multi-ring arrangements formed by electronically bundling the two-dimensional array transducer elements 29, 29, . . . of said probe 20 in concentric rings, is divided into a plural number of regions in radial form from the center to the outside; and, between the diameter of each divided region, the delay error (focusing error) due to the presence of a sound speed non-uniformity part (refer to 11 in FIG. 7) in the object is measured to the correct beam.

A probe according to this first embodiment has transducer elements arranged two-dimensionally. Although this is omitted in FIG. 2, actually they are arrayed with a matrix arrangement in the directions X and Y as shown in FIG. 4. The transducer elements are electronically bundled into a ring shape to form a circular pattern of annular array (multi-ring). This circular pattern is moved in the X direction or Y direction according to a cycle of transmitting/receiving for performing a linear scanning or a convex scanning with an ultrasonic beam, or sector scanning with the beam without moving the circular pattern. With such linear scanning, convex scanning, or sector scanning, with this two-dimensional probe, image data of a three-dimensional volume is acquired from the object. This image data is taken into scan converter 26 and transformed to the image data which is displayed on the screen of the monitor 27 as an ultrasonic slice image or a three-dimensional ultrasonic image.

Figure 2:
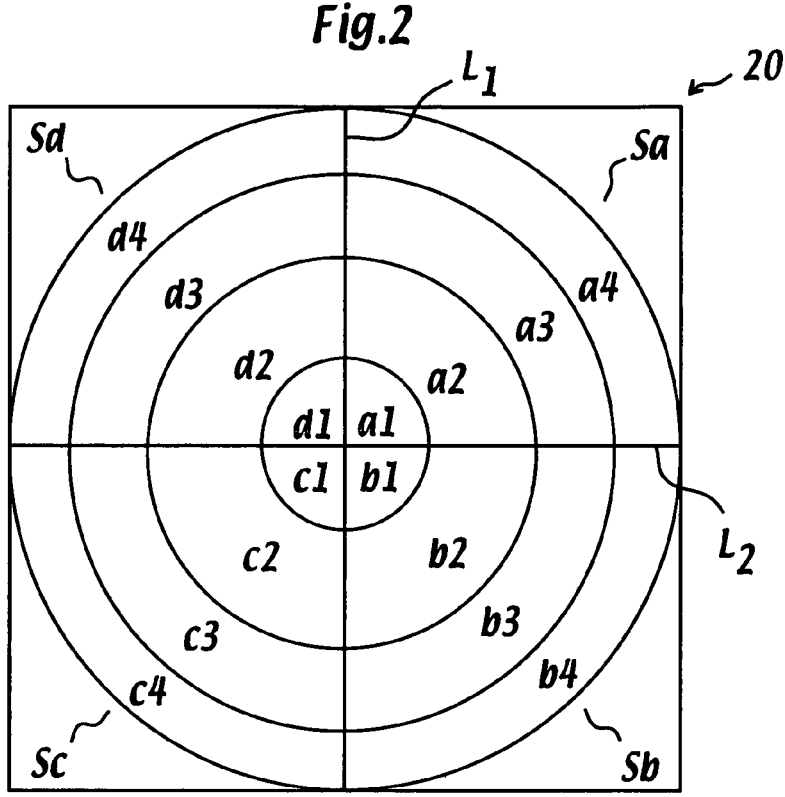
FIG. 2 is a diagram of a probe used in the first embodiment of the present invention.

To provide a simple illustration, a basic circular pattern for acquiring one image is shown in FIG. 2. In FIG. 2, the circular pattern composed of a multi-ring arrangement is effected by bundling said two-dimensional array transducer elements electronically in concentric rings so that the circular pattern is divided into a plural number of regions in radial form from the center to the outside. For example, element selecting data is transferred from element selecting data part 21 shown in FIG. 1 to switching control part 32. With the controlling of said switching control part 32, the dividing lines $L_1$, $L_2$ crossing the center of said multi-ring arrangement are formed, and these dividing lines $L_1$, $L_2$ divide the multi-ring arrangement into four sectors Sa, Sb, Sc, Sd.

Each of the divided sectors Sa~Sd is respectively connected to transmitting part 22 and beam-forming part 23, as shown in FIG. 1. And, to the multi-rings separated in each sector, delay data calculated on the condition that the speed of sound is uniform in medium 7 (refer to FIG. 6) is added. That is to say, in FIG. 2, transmitting part 22 and beam-forming part 23 are connected respectively to ring sections $a_1, a_2, a_3, a_4$; $b_1, b_2, b_3, b_4$; $c_1, c_2, c_3, c_4$; $d_1, d_2, d_3, d_4$ in each of the divided sectors Sa~Sd. Thus, delay control is performed individually for the respective divided rays. Accordingly, the ultrasonic beam is focused at some point with the prescribed delay.

Figure 6:
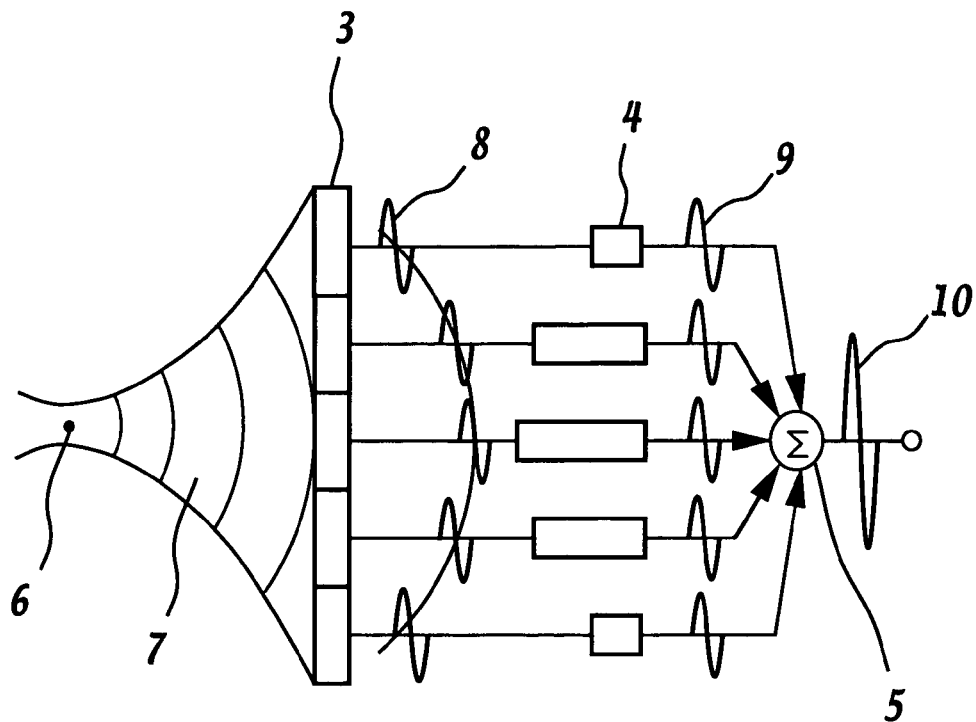
FIG. 6 is a diagram showing the formation of a traditional ultrasonic beam.
Figure 7:
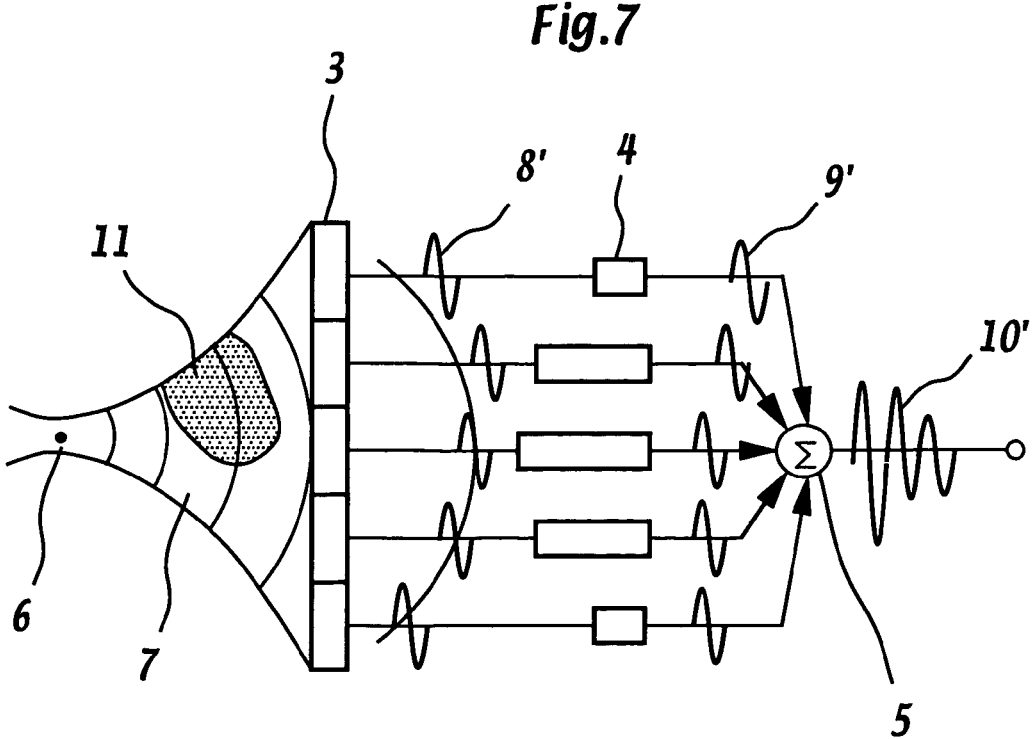
FIG. 7 is a diagram showing the beam formation in a case where a sound speed non-uniformity part is present in the medium when said ultrasonic beam is formed.

At this time, if the speed of sound in medium 7 is consistent with the speed of sound when the delay data is calculated, then the received signal increases in amplitude with the same phase adding because the phase surface in the received signal after receiving phasing is the same phase as the case shown in FIG. 6. On the other hand, if a sound speed non-uniformity part 11 exists in medium 7, then the received signal will be small because the phase surface in the received signal after receiving phasing is different, as shown in FIG. 7.

Figure 8:
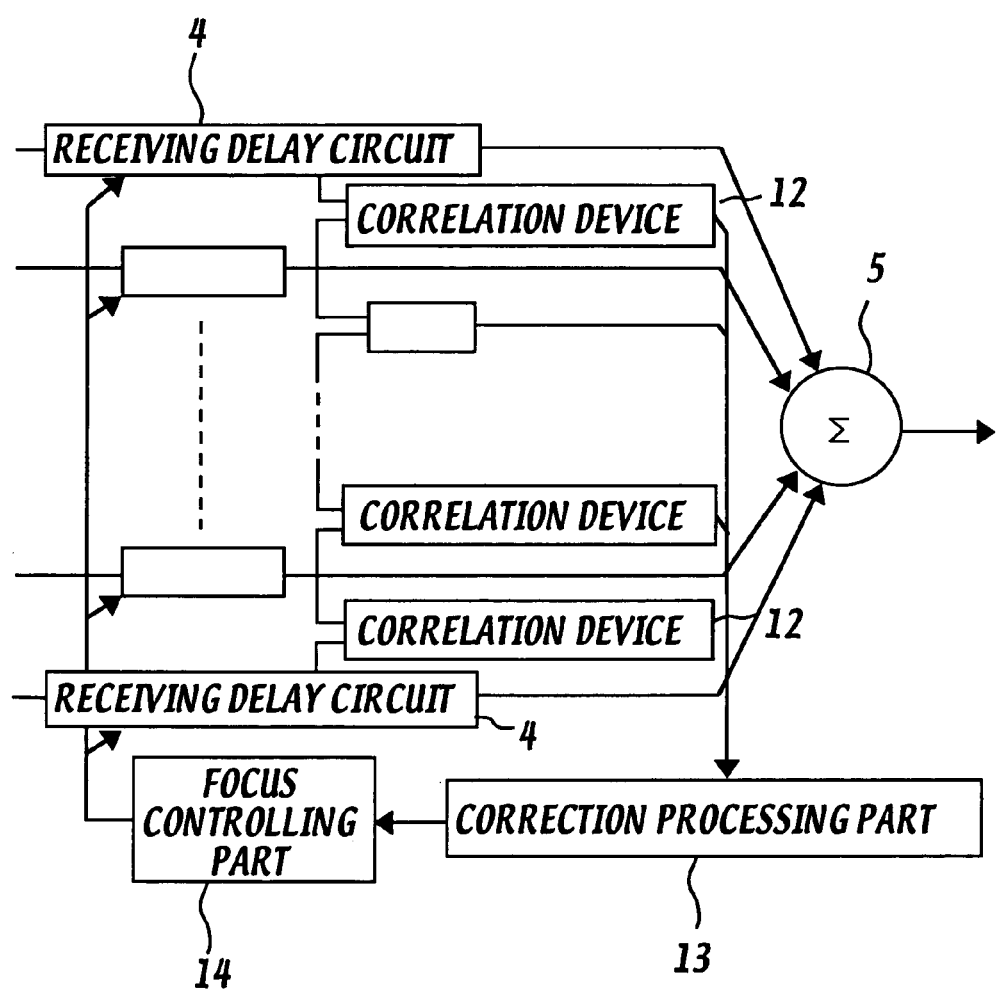
FIG. 8 is a block diagram showing a circuit arrangement for correcting the delay amount by using a mutual correlation method for producing adaptive image processing.

In accordance with the present invention, as shown in FIG. 2, the multi-ring arrangement is divided into, for example, four sectors Sa~Sd, so that the phase error (this corresponds to focusing error) is calculated with respect to the correlation of received signals after receiving phasing between the channel of transducer elements in each divided sector and is corrected in the same manner as shown in FIG. 8. That is to say, to each received signal after receiving phasing, the phase difference is calculated by mutual correlation between adjacent sectors in each ring divided in each sector Sa~Sd, as shown in FIG. 2, and correlation processing is performed between each ring in each sector.

For example, in FIG. 2, in the multi-ring arrangement divided into four sectors Sa~Sd, mutual correlation processing is performed between adjacent sectors, such as $a_1$ and $b_1$, $b_1$ and $c_1$, $c_1$ and $d_1$, $d_1$ and $a_1$ in the most interior ring. In addition, mutual correlation processing is performed between adjacent sectors, such as $a_2$ and $b_3$, $b_2$ and $c_2$, $c_2$ and $d_2$, $d_2$ and $a_2$ in the second ring. Furthermore, in the third and the fourth rings as well, mutual correlation processing is performed between adjacent sectors. Also, to acquire a relationship between each ring in each sector, the correlation processing between adjacent rings $a_1$ and $a_2$, $a_2$ and $a_3$, $a_3$ and $a_4$ in sector Sa is performed. In the sector Sb, the correlation processing is performed between adjacent rings $b_1$ and $b_2$, $b_2$ and $b_3$, $b_3$ and $b_4$. Furthermore, in sectors Sc, Sd as well, correlation processing is performed between adjacent rings. In this regard, the method of correlation processing is not restricted to the above-described sequence. Other methods can be used.

Figure 9:
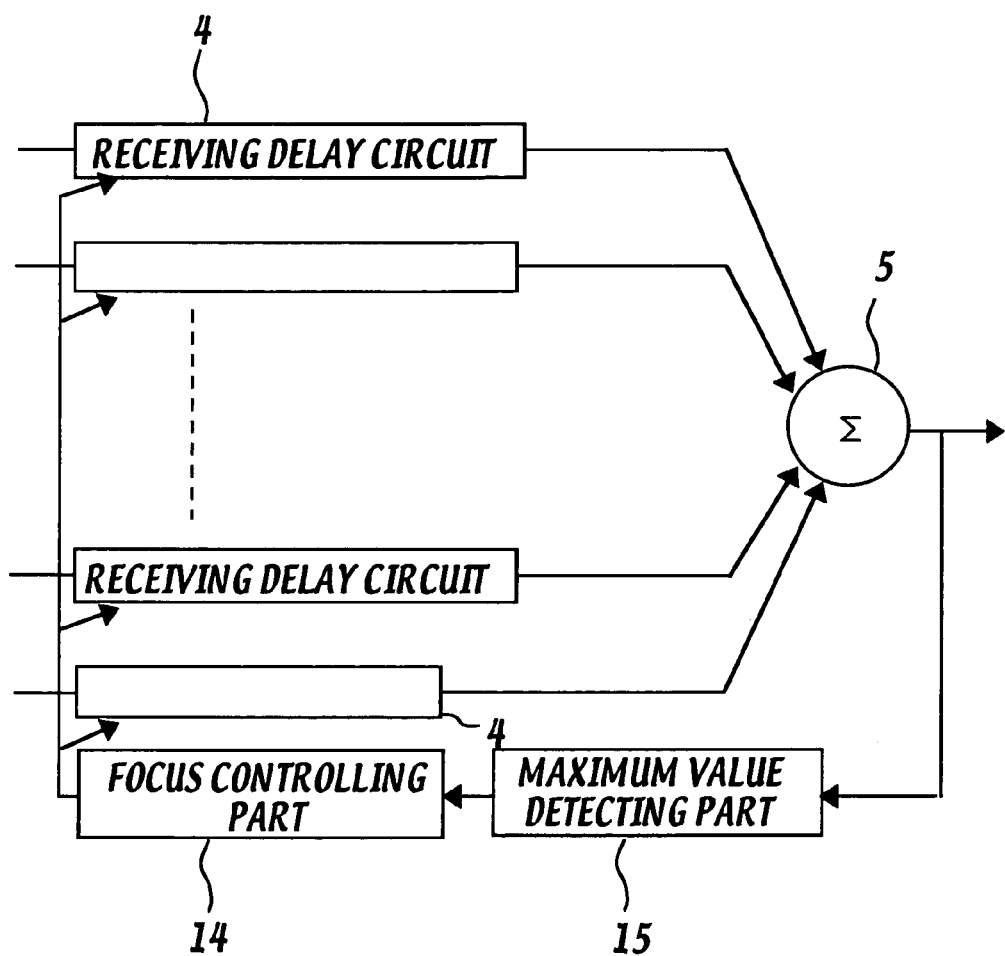
FIG. 9 is a block diagram showing a circuit arrangement for correcting the delay amount by using a maximum value brightness method for producing an adaptive image processing.

On the other hand, it is preferable to correct the phase error by calculating the delay amount that brings about maximum intensity by changing the delay amount of the beam-forming part between channels of transducer elements in each divided sector in the same way as shown in FIG. 9, under the condition that, for example, a multi-ring arrangement is divided into four sectors Sa~Sd, as shown in FIG. 2. That is, it is preferable to correct the phase error by calculating the delay amount that brings about a maximum intensity by changing the delay amount consecutively to each ring, which is divided into each sector Sa~Sd, $a_1$, $a_2$, $a_3$, $a_4$; $b_1$, $b_2$, $b_3$, $b_4$; $c_1$, $c_2$, $c_3$, $c_4$; $d_1$, $d_2$, $d_3$, $d_4$.

Next, a second embodiment of the present invention will be described. In this second embodiment, it is preferable to form a bundled circular pattern which is different from the circular pattern formed by bundling transducer elements arrayed two-dimensionally in said probe 20 to form a multi-ring arrangement having concentric rings, and to measure delay error due to the presence of a sound speed non-uniformity part in the object between each circular pattern (refer to 11 in FIG. 7) and to correct the beam.

Figure 3:
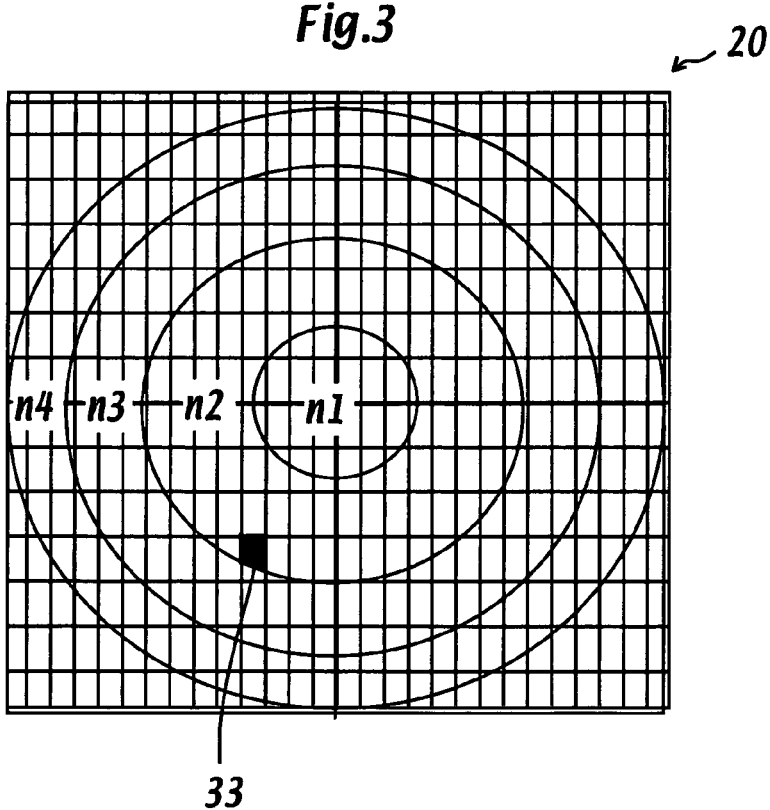
FIG. 3 is a diagram of a probe used in the second embodiment of the present invention.
Figure 5:
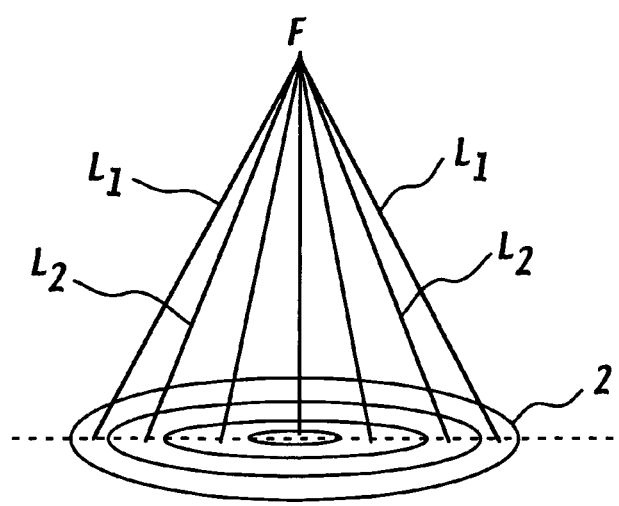
FIG. 5 is a diagram showing a principal of said multi-ring arrangement.

FIG. 3 is a diagram of a probe representing the second embodiment. This probe has a two-dimensional array of transducer elements. Each transducer element is connected to a respective delay circuit, and an ideal delay is given for some focus point to calculate delay error by correlating the outputs of the transducer elements. In the same way as shown in FIG. 5, when a multi-ring arrangement is bundled, if the bundled transducer elements forming one ring are formed, for example, such that the difference in the travel time (distance) of the ultrasound to the focus point F is in the range of/10 (is wave-length of the ultrasonic beam), then the delay error is corrected by adding said calculated delay error to the travel time.

For example, it is assumed that a specified transducer element 33 has a delay error in the multi-ring arrangement n1, n2, n3, n4 shown in FIG. 3. Although transducer element 33 is bundled into ring n2 in the ideal state, when the delay error is added to it, a correction is performed such that it is bundled into ring n3, whereby the delay error is corrected. And, after having calculated a correction value of delay error, the transducer element 33 is bundled so as to return to the ring in the original ideal state. Thus, it is not the diameter for forming an ultrasonic beam actually (bundled ring n1~n4), but the delay error that is detected with transducer element in another bundled ring. And, the correction is performed so as to form the bundled ring in consideration of the delay error.

In the case mentioned above, if a transmitter and a beam-forming circuit are connected to all of the two-dimensional array transducer elements, as shown in FIG. 3, then the circuit scale is large. Thus, for example, it is preferable to bundle adjacent transducer elements into rectangular blocks and connect the transmitter and the beam-forming circuits to bundled transducer elements as a unit. In addition, also in the second embodiment, it is preferable to correct the phase error by calculating the delay amount in which the output signal is a maximum value by changing the delay amount of the beam-forming part, as shown in FIG. 9.

As thus described, the present invention comprises means for measuring focusing error which occurs due to the presence of a sound speed non-uniformity part in the object and for correcting one or both of bundling or delay time of the multi-ring arrangement having two-dimensional array transducer elements in concentric rings. Thus, the interior of the object can be imaged with a corrected beam, so that the image quality of the ultrasonic image is improved.

The invention claimed is:

1. An ultrasonic diagnostic apparatus comprising a probe having two-dimensional array of transducer elements for transmitting and receiving ultrasonic waves to an object to be examined, in which a circular pattern of transducer elements is formed for transmitting and receiving an ultrasound signal by bundling the transducer elements of said two-dimensional array electronically to compose a multi-ring arrangement of transducer elements in concentric rings, and an ultrasound beam is transmitted and received with application of a delay time between each ring of said multi-ring arrangement, wherein said ultrasonic diagnostic apparatus further comprises means for transmitting and receiving an ultrasonic beam that has been corrected using said multi-ring arrangement by measuring a focusing error due to the presence of a sound speed non-uniformity interior of said object and modifying at least one of the manner of bundling of said multi-ring arrangement or the delay time based on the measuring error, and means for imaging the object with an echo signal formed of the corrected ultrasonic beam, wherein the multi-ring arrangement of transducer elements formed by bundling transducer elements of the two-dimensional array in said probe in concentric rings is divided into a plural number of sections in a radial shape from the center to the outside of the circular pattern, and a focusing error due to the presence of a sound speed non-uniformity part in the object is measured between each section of the divided circular pattern or each section of the concentric rings, and the ultrasonic beam is corrected by feeding back a measured value to delay circuits in said transmitting and receiving means.

2. An ultrasonic diagnostic apparatus according to claim 1, wherein the measuring of focusing error includes correcting a phase error by calculating a delay amount that brings about a maximum intensity by changing the delay amount consecutively to each ring.

3. An ultrasonic diagnostic apparatus comprising a probe having two-dimensional array of transducer elements for transmitting and receiving ultrasonic waves to an object to be examined, in which a circular pattern of transducer elements is formed for transmitting and receiving an ultrasound signal by bundling the transducer elements of said two-dimensional array electronically to compose a multi-ring arrangement of transducer elements in concentric rings, and an ultrasound beam is transmitted and received with application of a delay time between each ring of said multi-ring arrangement, wherein said ultrasonic diagnostic apparatus further comprises means for transmitting and receiving an ultrasonic beam that has been corrected using said multi-ring arrangement by measuring a focusing error due to the presence of a sound speed non-uniformity interior of said object and modifying at least one of the manner of bundling of said multi-ring arrangement or the delay time based on the measuring error, and means for imaging the object with an echo signal formed of the corrected ultrasonic beam, wherein a bundled arrangement of transducer elements is provided that is different from that of said multi-ring arrangement composed by bundling said transducer elements of said two-dimensional array of said probe in concentric rings, and a focusing error due to the presence of a sound speed non-uniformity part in the object is measured between each circular pattern, and the ultrasonic beam is corrected by feeding back a measured value to delay circuits in said transmission and receiving means and returning the multi-ring arrangement to an initial setting.

4. An ultrasonic diagnostic apparatus according to claim 3, wherein the measuring of focusing error includes correcting a phase error by calculating a delay amount that brings about a maximum intensity by changing the delay amount consecutively to each ring.

5. An ultrasonic diagnostic apparatus comprising:
a probe having a two-dimensional array of transducer elements;
transducer selection means for electronically bundling transducer elements into a multi-ring arrangement of a circular pattern composed of a plural number of rings, said multi-ring arrangement of transducer elements formed by bundling transducer elements of the two-dimensional array in said probe in concentric rings being divided into a plural number of sections in a radial shape from a center to an outside of the circular pattern;
means for calculating a focusing error between sections in said multi-ring arrangement;
means for feed-back correcting said calculated focusing error relative to a set delay time to produce a corrected focusing error signal;
means for beam-forming comprised of delay circuits for applying a delay time to each ring of said multi-ring arrangement of transducer elements in response to a corrected focusing error signal and an adder circuit for adding the outputs of said each delay circuits; and
means for imaging an output signal of said means for beam-forming.

6. An ultrasonic diagnostic apparatus according to claim 5, wherein means for calculating the focusing error between sections in said multi-ring arrangement includes means for calculating the focusing error between rings in one section.

7. An ultrasonic diagnostic apparatus according to claim 5, wherein the means for calculating the focus error includes means for correcting a phase error by calculating a delay amount that brings about a maximum intensity by changing the delay amount consecutively to each ring.

8. An ultrasonic diagnostic apparatus comprising:
transducer selection means for initially forming a multi-ring arrangement of transducer elements composed of a plural number of rings from a two-dimensional array of transducer elements;
means for specifying transducer elements having a focusing error in each ring of said multi-ring arrangement;
ring correction means for changing a specified transducer element to a different ring from initial ring location to correct the focusing error;
a beam-forming part comprised of delay circuits for applying a delay time to the transducer elements of each ring of said multi-ring arrangement and an adder circuit for adding the outputs of each of said delay circuits; and
means for imaging an output signal of said beam-forming part.

9. Ultrasonic diagnosing apparatus according to claim 8, wherein means for specifying transducer elements having a focusing error includes means for bundling a group of adjacent transducer elements different from a ring and assigning a transmitter and beam-forming circuit to this bundled transducer group.

10. An ultrasonic diagnostic apparatus according to claim 8, further comprising means for correcting a phase error by calculating a delay amount that brings about a maximum intensity by changing the delay amount consecutively to each ring.

11. An ultrasonic diagnostic apparatus comprising:
a probe having a two-dimensional array of transducer elements arranged in a circular pattern so as to produce a multi-ring arrangement of transducer elements formed by bundling transducer elements of the two-dimensional array in said probe in concentric rings which are divided into a plural number of sections in a radial shape from a center to an outside of the circular pattern;
means for calculating a focusing error between sections of the concentric rings;
means for feed-back correcting said calculated focusing error relative to a set delay time to produce a corrected focusing error signal;
means for beam-forming comprised of delay circuits for applying a delay time each ring of said multi-ring arrangement of transducer elements in response to a corrected focusing error signal and an adder circuit for adding the outputs of said each delay circuits; and
means for imaging an output signal of said means for beam-forming.

12. An ultrasonic diagnostic apparatus according to claim 11, wherein the means for calculating the focus error includes means for correcting a phase error by calculating a delay amount that brings about a maximum intensity by changing the delay amount consecutively to each ring.

* * * * *